United States Patent
Chen et al.

(10) Patent No.: US 9,202,961 B2
(45) Date of Patent: Dec. 1, 2015

(54) IMAGING DEVICES WITH SOLID-STATE RADIATION DETECTOR WITH IMPROVED SENSITIVITY

(71) Applicant: Redlen Technologies, Saanichton (CA)

(72) Inventors: Henry Chen, Victoria (CA); Salah Awadalla, Victoria (CA); Pinghe Lu, Victoria (CA); Pramodha Marthandam, Victoria (CA)

(73) Assignee: REDLEN TECHNOLOGIES, Saanichton (CA)

( * ) Notice: Subject to any disclaimer, the term of this patent is extended or adjusted under 35 U.S.C. 154(b) by 202 days.

(21) Appl. No.: 13/910,358

(22) Filed: Jun. 5, 2013

(65) Prior Publication Data

US 2013/0266114 A1 Oct. 10, 2013

Related U.S. Application Data

(63) Continuation-in-part of application No. 12/364,042, filed on Feb. 2, 2009, now Pat. No. 8,614,423.

(51) Int. Cl.
*G01T 1/24* (2006.01)
*H01L 31/00* (2006.01)
*H01L 31/08* (2006.01)
(Continued)

(52) U.S. Cl.
CPC .............. *H01L 31/085* (2013.01); *G01N 23/046* (2013.01); *G01T 1/241* (2013.01); *H01L 27/14618* (2013.01); *H01L 27/14658* (2013.01); *H01L 31/0224* (2013.01);
(Continued)

(58) Field of Classification Search
CPC .............. H01L 31/082; H01L 31/0224; H01L 31/1832; H01L 27/14618; H01L 27/14658; G01T 1/241; G01N 23/046; Y02E 10/50
USPC ...................................................... 250/363.04
See application file for complete search history.

(56) References Cited

U.S. PATENT DOCUMENTS

| 4,301,368 A | 11/1981 | Riihimaki |
| 4,858,856 A | 8/1989 | Cloth |

(Continued)

FOREIGN PATENT DOCUMENTS

| EP | 1 156 347 A1 | 11/2001 |
| JP | 01-077969 A | 3/1989 |

(Continued)

OTHER PUBLICATIONS

International Search Report and Written Opinion, Intl. Application PCT/US2010/021142. International Searching Authority—Korean Intellectual Property Office (ISA/KR), Aug. 13, 2010.

(Continued)

*Primary Examiner* — Yara B Green
(74) *Attorney, Agent, or Firm* — The Marbury Law Group PLLC

(57) ABSTRACT

A radiation detector includes a semiconductor substrate having opposing front and rear surfaces, a cathode electrode located on the front surface of the semiconductor substrate configured so as to receive radiation, and a plurality of anode electrodes formed on the rear surface of said semiconductor substrate. A work function of the cathode electrode material contacting the front surface of the semiconductor substrate is lower than a work function of the anode electrode material contacting the rear surface of the semiconductor substrate.

25 Claims, 13 Drawing Sheets

(51) Int. Cl.
*G01N 23/04* (2006.01)
*H01L 31/18* (2006.01)
*H01L 31/0224* (2006.01)
*H01L 27/146* (2006.01)

(52) U.S. Cl.
CPC .... *H01L 31/1832* (2013.01); *H01L 2924/0002* (2013.01); *Y02E 10/50* (2013.01)

(56) References Cited

U.S. PATENT DOCUMENTS

| | | | |
|---|---|---|---|
| 5,100,767 | A | 3/1992 | Yanagawa et al. |
| 5,368,882 | A | 11/1994 | Tran et al. |
| 5,608,188 | A | 3/1997 | Choon et al. |
| 5,616,925 | A | 4/1997 | Rhiger et al. |
| 5,677,539 | A | 10/1997 | Apotovsky |
| 5,905,264 | A | 5/1999 | Shahar et al. |
| 5,933,706 | A | 8/1999 | James et al. |
| 6,034,373 | A | 3/2000 | Shahar et al. |
| 6,037,595 | A | 3/2000 | Lingren |
| 6,043,106 | A | 3/2000 | Mescher et al. |
| 6,046,068 | A | 4/2000 | Orava et al. |
| 6,069,360 | A | 5/2000 | Lund |
| 6,175,120 | B1 | 1/2001 | Mcgregor et al. |
| 6,215,123 | B1 | 4/2001 | Orava et al. |
| 6,329,658 | B1 | 12/2001 | Mestais et al. |
| 6,333,504 | B1 | 12/2001 | Lingren |
| 6,362,484 | B1 | 3/2002 | Beyne et al. |
| 6,399,951 | B1* | 6/2002 | Paulus et al. ............. 250/370.13 |
| 6,410,922 | B1 | 6/2002 | Spartiotis et al. |
| 6,465,860 | B2 | 10/2002 | Shigenaka et al. |
| 6,483,099 | B1 | 11/2002 | Yu et al. |
| 6,510,195 | B1 | 1/2003 | Chappo et al. |
| 6,524,966 | B1 | 2/2003 | Wright et al. |
| 6,694,172 | B1 | 2/2004 | Gagnon et al. |
| 6,765,213 | B2 | 7/2004 | Shahar et al. |
| 6,781,132 | B2 | 8/2004 | Mcgregor |
| 7,038,288 | B2 | 5/2006 | Lai et al. |
| 7,223,982 | B1 | 5/2007 | Chen et al. |
| 7,247,860 | B2 | 7/2007 | Yanagita et al. |
| 7,462,833 | B2 | 12/2008 | Chen et al. |
| 2001/0035497 | A1 | 11/2001 | Montemont et al. |
| 2002/0066531 | A1 | 6/2002 | Ke et al. |
| 2002/0182716 | A1 | 12/2002 | Weisbuch et al. |
| 2003/0034456 | A1* | 2/2003 | McGregor ............. 250/370.09 |
| 2004/0033641 | A1 | 2/2004 | Yang et al. |
| 2005/0023475 | A1 | 2/2005 | Li et al. |
| 2005/0189474 | A1 | 9/2005 | Tomioka |
| 2005/0199816 | A1 | 9/2005 | Amemiya et al. |
| 2005/0247882 | A1 | 11/2005 | Wear et al. |
| 2006/0186501 | A1 | 8/2006 | Ishimura |
| 2006/0255280 | A1 | 11/2006 | Shibayama |
| 2007/0194243 | A1 | 8/2007 | Chen et al. |
| 2008/0042070 | A1 | 2/2008 | Levin |
| 2008/0149844 | A1 | 6/2008 | Chen et al. |
| 2008/0258066 | A1 | 10/2008 | Chen et al. |
| 2008/0304622 | A1* | 12/2008 | Morton ............. 378/51 |
| 2010/0296625 | A1* | 11/2010 | Wainer et al. ............. 378/19 |

FOREIGN PATENT DOCUMENTS

| | | |
|---|---|---|
| JP | 06-112515 A | 4/1994 |
| JP | 07-325157 A | 12/1995 |
| JP | 11-163310 A | 6/1999 |
| JP | 2005-257437 A | 9/2005 |
| JP | 2006-237186 A | 9/2006 |
| KR | 10-2002-0035052 A | 5/2002 |

OTHER PUBLICATIONS

Jahnke et al., "Signal formation and decay in CdTe x-ray detectors under intense irradiation," Med. Phys., Jan. 1999, 26(1):38-48.

Kim et al,. "Schottky-type polycrystalline CdZnTe X-ray detectors," Current Applied Physics, 2009, 9:306-310.

Sudharsanan et al., "Performance of P-I-N. CdZnTe Radiation Detectors and Their Unique Advantages," Mat. Res. Soc. Symp. Proc., 1998, 487:245-255.

Takahashi et al., "High-resolution Schottky CdTe diode for hard X-ray and gamma-ray astronomy," Nuclear Instruments and Methods in Physics Research A, 1999, 436:111-119.

"Photoelectric Effect Lab" Retrieved from Internet [Jan. 19, 2012], Retrieved from url http://physics.nyu.edu/~physlab/Modern_1/Photoelectric.pdf; published Nov. 14, 2002.

* cited by examiner

IMAGING DEVICES WITH SOLID-STATE RADIATION DETECTOR WITH IMPROVED SENSITIVITY

CROSS-REFERENCE TO RELATED APPLICATIONS

This application is a continuation-in-part of U.S. patent application Ser. No. 12/364,042 filed Feb. 2, 2009, which is hereby incorporated herein by reference in its entirety.

BACKGROUND OF THE INVENTION

The present invention generally relates to detectors for gamma-ray and X-ray detection devices.

SUMMARY OF THE INVENTION

One embodiment of the invention relates to a radiation detector comprising a semiconductor substrate having opposing front and rear surfaces, a cathode electrode located on the front surface of said semiconductor substrate configured so as to receive radiation, and a plurality of anode electrodes formed on the rear surface of said semiconductor substrate. The work function of the cathode electrode material contacting the front surface of the semiconductor substrate is lower than the work function of the anode electrode material contacting the rear surface of the semiconductor substrate.

Another embodiment of the present invention is a radiation detector system comprising a semiconductor substrate having opposing front and rear surfaces, a cathode electrode located on the front surface of said semiconductor substrate configured so as to receive radiation, a plurality of anode electrodes formed on the rear surface of said semiconductor substrate, and a means for applying a forward bias to the detector during operation such that the anode electrodes is maintained at a higher potential than the cathode electrode and such that the signal is collected from the anode electrodes. The work function of the cathode electrode material contacting the front surface of the semiconductor substrate is lower than the work function of the anode electrode material contacting the rear surface of the semiconductor substrate.

Finally, another embodiment relates to a method of operating a radiation detector comprising the steps of: a) providing a radiation detector comprising a semiconductor substrate having opposing front and rear surfaces, a cathode electrode located on the front surface of said semiconductor substrate configured so as to receive radiation, and a plurality of anode electrodes formed on the rear surface of said semiconductor substrate; b) receiving radiation at the cathode electrode; c) applying a forward bias to detector to maintain the anode electrodes at a higher potential than the cathode electrode; and, d) collecting a signal from the anode electrodes.

DETAILED DESCRIPTION OF THE PREFERRED EMBODIMENTS

Figure 1:
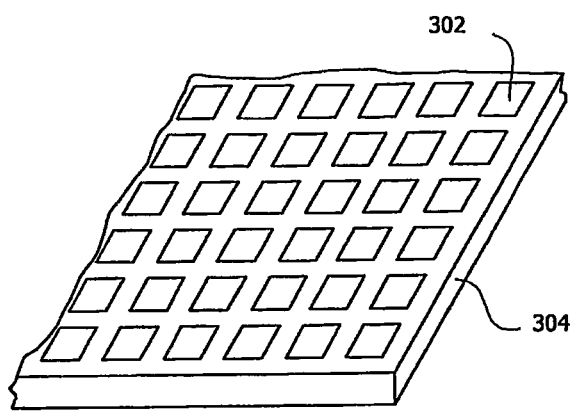
FIG. 1 is a perspective view of a CZT substrate with anode electrode pixels.

The following definitions are used herein:

Cathode electrode: the electrode on one major surface of the detector substrate where incident gamma rays or x-rays enter the detector, i.e. positioned towards the radiation source.

Anode electrodes: segmented electrode contacts located on the rear surface of the substrate, i.e. positioned away from the radiation source.

Forward-bias: The application of an electric potential between the anode and cathode electrical contacts with the anode exposed to a higher potential and cathode experiencing a lower potential. A forward-bias, as used herein, means that the anode is the electrode from which electric signals, such as voltage or current generated by incident gamma rays or x-rays entering the detector, are collected.

Interpixel or inter pixel: the region or gap separating pixel electrodes. For electrode configurations with non-pixellated discrete contact segments the term is equivalently applied to the gap between contact segments.

Solder mask: a coating on the semiconductor detector or on the printed circuit board ("PCB"), which is designed to insulate and protect either the segmented anode (pixels) on the semiconductor detector or the mating metal pads on the PCB, keeping them from shorting during PCB-attachment process. The solder mask may have any suitable color, such as a dark green/blue color and occasionally a yellowish color.

Embodiments of the present invention describe radiation detectors, such as metal-semiconductor-metal (MSM) or heterojunction metal/semiconductor type detector with improved sensitivity. In other words, the detector preferably does not contain a p-i-n or p-n diode (i.e., no semiconductor p-n junction) formed in a semiconductor substrate or tile. In fact, radiation detectors of the embodiments of the present invention provide the additional benefit of room temperature operation without the need of cooling as usually required for p-i-n heterojunction devices. The embodiments of the invention provide the benefit of increased detector sensitivity while also maintaining other beneficial properties such as lower leakage current and high detector energy resolution. Additionally, the embodiments of the invention may offer the further benefit of being reliable and suitable for mass production. In one embodiment, a radiation detector comprises a semiconductor substrate having opposing front and rear surfaces, a cathode electrode located on the front surface of said semiconductor substrate configured so as to receive radiation, and a plurality of anode electrodes formed on the rear surface of said semiconductor substrate. Preferably, the work function of the cathode electrode material contacting the front surface of the semiconductor substrate is lower than the work function of the anode electrode material contacting the rear surface of the semiconductor substrate. It is important to note herein that prior-art radiation detector devices, such as that disclosed in for example T. Takahashi et al., "High-resolution Schottky CdTe diode for hard X-ray and gamma-ray astronomy", Nuclear Instruments & Methods in Physics Research A 436 (1999) 111-119, have instead utilized indium as the anode electrode material rather than as the cathode electrode material, and apply forward and reverse bias so that the induced signal is collected from the anode and cathode, respectively. For example, a positive bias is placed on the In anode in the device disclosed in the work of T. Takahashi et al. However, signal collection at the anode with indium as the anode electrode material does not present the increased photo-peak count sensitivity benefits of the configuration of the embodiments of the present invention.

Radiation detectors can be configured in a variety of ways. A common configuration comprises a cathode electrode and a plurality of anode electrodes located on opposite sides of a semiconductor plate or substrate. Typically these radiation detectors have pixilated anode electrode arrays fabricated by various deposition and lithography processes resulting in a gap between pixels, termed the interpixel gap or interpixel region. In an exemplary embodiment of the present invention, the interpixel gap has a width of between 100 and 500 µm. More preferably, the interpixel gap width is between 200 and 400 µm.

In the preferred embodiments, the radiation detectors comprise a semiconductor material, such as a semiconductor material preferably comprising CdZnTe (CZT) or CdTe, having opposing front and rear surfaces and lacking a p-n or p-i-n junction. Although other types of semiconductor materials exemplified by lead iodide, thallium bromide, gallium arsenide or silicon may be used.

More preferred is $Cd_{(1-x)}Zn_xTe$ (where x is less than or equal to 0.5), a wide band gap ternary II-VI compound semiconductor with unique electronic properties. This type of semiconductor is useful in gamma-ray and X-ray detectors which are used as spectrometers that operate at room temperature for nuclear radiation detection, spectroscopy and medical imaging applications.

Additionally, in the preferred embodiments, the radiation detectors comprise a cathode electrode located on the front surface of said semiconductor substrate configured so as to receive radiation, and a plurality of anode electrodes formed on the rear surface of said semiconductor substrate. The work function of the cathode electrode material is preferably less than about 4.5 eV while the work function of the anode electrode material is preferably more than or equal to about 4.8 eV. A cathode electrode material having a work function of less than about 4.5 eV may, for example, be selected from the group comprising one of In, Al, and Ti and alloys thereof. An anode electrode material having a work function of more than or equal to about 4.8 eV may, for example, be selected from the group comprising one of Au, Pt and other noble metals and their alloys. In the embodiments of the present invention, by utilizing a cathode electrode material with a low work-function, such as a work function less than about 4.5 eV, for example, a cathode electrode material comprising indium, a higher density of charge injection, namely electron injection, occurs at the metal/semiconductor interface from the cathode.

In operation, the anode and cathode of the preferred embodiments is electrically connected to a voltage source. The anode is exposed to a higher potential than the cathode, for example, by applying a positive voltage to the anode while the cathode is grounded or by applying a negative voltage to the cathode and virtually grounding the anode.

Illustrated in FIG. 1, is an example of pixellated anode electrodes 302 formed on a semiconductor substrate 304, such as a CZT substrate (also referred to as a "tile"). The cathode electrode is formed on the bottom side of the substrate 304.

Figure 2A:
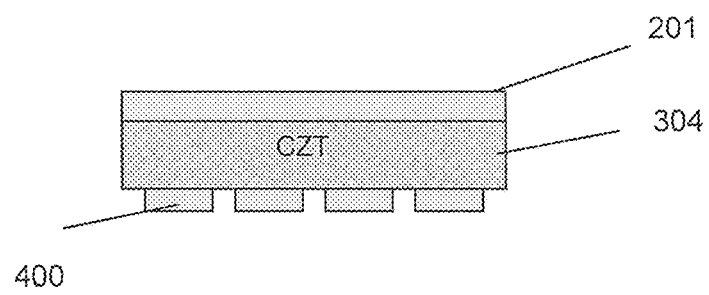
FIGS. 2A-D are schematic cross-sectional views of a method of making a detector with a housing.
Figure 2B:
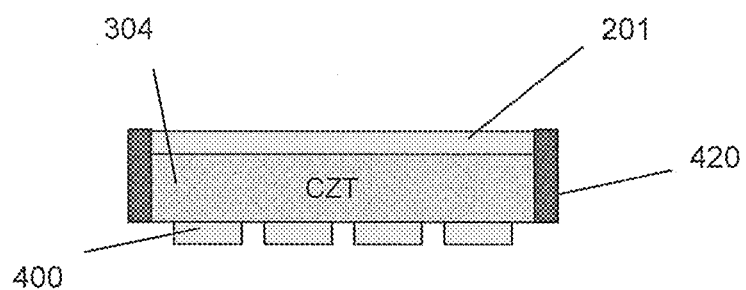

FIG. 2A shows the radiation detector device of an embodiment of the present invention containing anode electrode pixels 400 on a rear side of a CZT substrate 304, and containing cathode electrode 201 on a front side of the CZT substrate. Optionally, a protective coating 420 is applied to polished side edges of the CZT tile as shown in FIG. 2B. For example, the CZT tile may be dipped in a protective coating (such as solder mask) to cover the exposed sides and dried for at least 5 hours.

An optional housing is preferably formed separately and prior to attaching it to a radiation detector. The housing described in U.S. Pat. No. 7,462,833, which is hereby incorporated by reference, may be used as the optional housing. Accordingly, the method of making the detector of one embodiment comprises (a) providing a radiation detector comprising a semiconductor substrate having opposing front and rear surfaces, a cathode electrode located on the front surface of said semiconductor substrate and a plurality of anode electrodes on the rear surface of said semiconductor substrate, and wherein the work function of the cathode electrode material is lower than the work function of the anode electrode material, (b) providing a separately formed electrically conductive housing, and (c) attaching the housing to the cathode electrode such that the housing and the cathode electrode are in electrical contact. Alternatively, the optional housing may be omitted entirely or substituted with an optional printed circuit board type of cathode plate, such as a gridded PCB type of cathode plate.

A non-limiting example of a method of particular embodiment is depicted in FIGS. 2A-2D showing side cross-sectional views of the detector at various stages of attaching a housing thereto. Starting with FIG. 2A, a radiation detector and its basic elements, cathode electrode 201, semiconductor substrate 304 and anode electrodes 400 are shown. The anode and cathode electrodes may be formed in either order on substrate 304 as will be described in more detail in FIG. 3. The detector may or may not comprise at least one of a guard ring or screening electrode. Next, an optional protective coating (or solder mask) 420 is applied to edges of the substrate 304, as shown in FIG. 2B. Alternatively, this coating may be removed once a housing is formed thereon, resulting in an air gap between said housing and a side of the detector. Alternatively, this coating 420 is made of other electrically insulating materials, such as Humiseal.

Figure 2C:
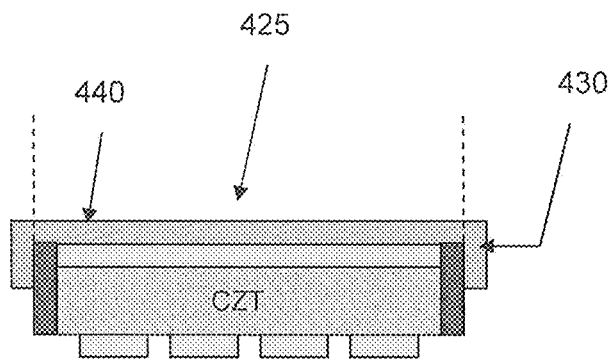

As shown in FIG. 2C, the electrically conductive housing is attached to the cathode and optionally the sides of the detector. In this illustration, the housing 425 comprises a top portion 440 and an optional side portion 430. The sides of the detector may or may not be glued to the protective coating (or solder mask) 420 covering sides of the detector depending on various reasons such as for example, if one wishes to later remove the protective coating. In this example, the housing is attached to the cathode via an epoxy, although one skilled in the art may chose from other adhesives.

The electrically conductive housing 425 shields the detector from background electromagnetic fields (or magnetic fields). Additionally, device electric fields are focused using this housing. The housing is also preferably transparent to X-ray or gamma-ray radiation. Further, the housing preferably exhibits little or no oxidation in ambient air, such as under normal operating conditions of the detector. As such, the housing is most preferably a thin structure and comprises a material transparent to radiation, substantially impervious to background electromagnetic fields and exhibits little or no oxidation at ambient conditions.

For example the housing may be between about 50 microns and 100 microns thick. In some cases a metal foil is sufficient as a housing.

Based on the parameters set forth above, one skilled in the art may chose from a host of materials for constructing the housing. In general, metals and metallic alloys are preferred. Any suitable metal which does not substantially oxidize in air may be used. A non-limiting example of suitable metallic alloys includes stainless steel, brass (such Ni/Ti coated brass), NiCo alloys, NiFe alloys, NiFeCo alloys, NiFeMo alloys or NiFeCuMo alloys. A class of metal alloys termed "Mu-metals" is most preferred. Mu-metals are a type of NiFe alloy, particularly effective at screening static or low frequency magnetic fields. In some cases, the aforementioned alloys may be doped with other alloying elements, mechanically pre-treated (e.g. cold worked, hot worked etc.), chemically surface-treated (e.g. surface coating for corrosion resistance) or any combination thereof.

In a particular embodiment, the housing for a radiation detector comprises a first means for electrically contacting a cathode electrode of a semiconductor radiation detector and a second means for shielding at least one side of a detector. For example, the first means may comprise the top portion 440 while the second means may comprise the side portion 430 of a housing 425. In some cases the side portion 430 extends over a fraction of the thickness of the semiconductor substrate, on at least one side. However, the side portion 430 may be omitted entirely. The top portion 440 is preferably shaped to make optimal electrical contact with a high voltage supply which is in electrical contact with the anodes and cathodes of the radiation detector, and preferably maintains the anode at a higher electrical potential relative to the cathode.

In some cases a flat top portion 440 is preferred. In another particular embodiment, the housing 425 is hemispherical or dome-shaped and partially or completely covers at least one side of the semiconductor substrate.

In some embodiments, the housing 425 is shaped to conform to geometry of the detector, more specifically, to geometry of the cathode, to which it is secured. Therefore, one skilled in the art may contemplate various curved or angular housing shapes given the shape of the detector. In a non-limiting example, the housing is a rectangular or circular-cross-sectioned (e.g. cylinder) shape.

When the housing is constructed to extend over (partially or completely) at least one side of the substrate, said at least one side is spaced from said housing. This gap is either empty or filled with an insulating material.

The housing 425 is attached to the cathode electrode 201 such that an electrical conduction path exists between the two. In a preferred case, the housing and the cathode are attached via an electrically conductive material. Most preferably, an electrically conductive polymeric material, such as a conductive epoxy applied to the inner face or surface of the housing is used.

Figure 2D:
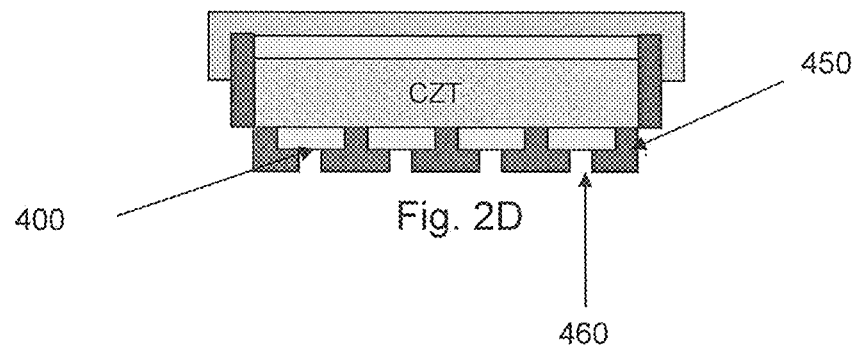

FIG. 2D illustrates an optional step where a solder mask 450 is disposed over the pixilated anode electrodes 400 providing mechanical protection while allowing external access to the electrodes. Further electrical isolation of the anode electrodes may be achieved with the solder mask 450 when the mask is formed between the pixilated anode electrodes 400 at the interpixel region.

Accordingly, a particular optional embodiment is directed to a radiation detector comprising a solder mask disposed above the anode electrodes in addition to the housing 425 contacting the cathode electrode 201. Solder masks suitable for embodiments of the present application are described in U.S. application Ser. No. 11/642,819, filed on Dec. 21, 2006 which is hereby incorporated by reference in its entirely.

Preferably, the solder mask is photoimageable such that the portions of the solder mask 450 material over the anodes 400 are directly exposed to radiation, such as UV radiation, through a mask. The radiation either cross links or uncross links the exposed portions of the solder mask, depending on the type of epoxy used (i.e., analogous to a positive or negative photoresist). The uncross linked portions are then selectively etched away to form the openings 460 exposing a portion of the anode 400 surfaces. Alternatively, for a non-photoimageable solder mask material, a conventional photoresist mask formed over the solder mask may be used in the patterning step. The entire radiation detector device is covered with the solder mask except for the cathode and the anode regions exposed through the opening. Preferably, only a portion of each anode 400 is exposed in each opening 460 and no portion of the tile 304 is exposed. Thus, the solder mask is used as a protective coating (i.e., passivation/encapsulation agent) for protecting the entire radiation detector device.

As described in U.S. application Ser. No. 11/642,819, the radiation detector device comprising a solder mask may be connected to a readout printed circuit board (PCB), at the underfill filling locations located on the mating pad. The solder balls are placed in the openings 460 formed in the solder mask which serve as electrical interconnects between anodes 400 of the detector device and the conductor pads of the printed circuit board.

FIGS. 3A-I illustrate, without any intent to limit the present embodiments, an example of steps in a method of forming tri-layer metal anode contacts on a semiconductor substrate at positions (pixels) for defining radiation detector cells with an interpixel gap with high resistivity between the detector cells. While tri-layer contacts are illustrated, it should be understood that single layer or bi-layer anode electrodes may also be used. In this example, it is assumed that the semiconductor substrate is made of cadmium zinc telluride (CdZnTe) or cadmium telluride (CdTe), although it will be appreciated that other semiconductor materials, for example lead iodide, thallium bromide, gallium arsenide or silicon, can be used. Also, it will be assumed that the metal used for the metallization layer and the contacts is gold, although it will be appreciated that other metal anode, alloys or other conductive materials, for example platinum, could be used instead.

Thus, FIGS. 3A-3I are a schematic cross-sectional views from the side of a detector substrate at various stages in the formation of gold anode contacts on a CdZnTe substrate. The detailed features and structure at each step of the process are shown, resulting in an array of anode contact pixels on the rear surface of the CZT (drawn as facing up in this illustration), and a single cathode electrode on the front surface of the CZT tile (drawn as facing down in this illustration). In this example, two additional contact layers are added on to the pixilated primary contact layer on the rear side, for improved device assembly. The process can be applied to any array size and pixel configuration for CZT devices. A typical device size is a 20×20×5 mm detector, having 8×8 pixels or 11×11 pixels depending on the application. As a precursor to contact fabrication, the CZT wafer is polished and etched such that high quality clean crystal surfaces are prepared for the deposition process.

Figure 3A:
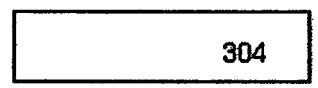
FIGS. 3A-I are schematic cross-sectional views of a method of making a detector at various stages in the formation of contacts thereon.

A direct lithography fabrication process is described with reference to FIGS. 3A-I, and for the case of the primary anode contact being gold, with two additional contact layers, and for separately forming of the cathode contact on the opposing side of the CZT tile or substrate 304 shown in FIG. 3A. It is noted, however, that direct lithography process for formation of the anode electrode is only one of many processes that may be used to form the electrodes. Other methods, including but not limited to a lift-off method, may be used to form the electrodes instead. For example, a lift-off method for forming the anode electrodes of the embodiments of the present invention comprises the steps of a) providing the substrate, b) forming a mask (such as a photoresist mask) over the substrate surface, where the pattern comprises portions of mask material and spaces without mask material, c) depositing an anode electrode material over the mask where first portions of the anode electrode material are formed on the substrate in the spaces of the mask pattern while second portions of the anode electrode material are formed on the mask material, and d) removing or lifting-off the mask such that second portions of the anode electrode material formed over the mask material are also removed with the mask, and first portions of the anode electrode material contacting the substrate remain on the substrate.

Figure 3B:
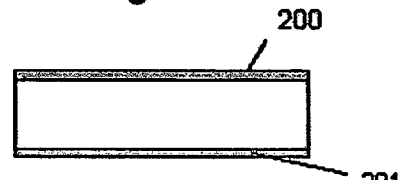

In step 1 of the direct lithography process, shown in FIG. 3B a primary layer of gold 200 is deposited onto a rear side of the CZT tile 304 (the rear side is shown facing up in FIG. 3B). The gold layer 200 may be deposited by electroless deposition. Alternatively the gold layer 200 may be deposited by other known techniques, such as sputtering or evaporation. Additionally, a cathode electrode layer 201 comprising indium is deposited by sputtering, electroless plating or other suitable method onto an opposing front side of the CZT tile. The CZT tiles are first cleaned in acetone, as is well known. The clean CZT tiles 304 are appropriately masked and placed in a chamber for sputtering or plating of gold onto a first side and indium onto a second side. Typical thickness of the deposited cathode layer may be between 10-100 nm. The deposited gold may be annealed at 90 deg C. for 15 minutes to increase adhesion to the substrate. An adhesion test can be done after a few hours using Scotch tape to confirm quality of the adhesion.

Figure 3C:
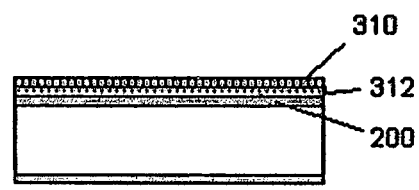

In an optional step 2 shown in FIG. 3C, two additional contact layers are deposited onto the rear side (anode side to be pixilated) of the tile, over the primary contact layer 200. In this example, a Ni layer 312 is deposited using sputtering or a thermal evaporation process to a thickness <100 nm and nominally 50 nm. Then another gold layer 310 is deposited using sputtering, thermal evaporation and/or an electroless process to a thickness <50 nm and nominally 20 nm. Alternative conductive contact material can be substituted for either or both of the additional contact layers.

Figure 3D:
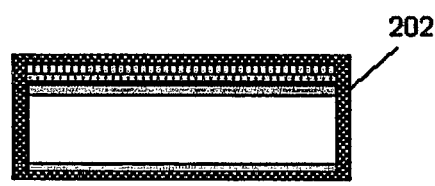

In step 3, as shown in FIG. 3D, a photoresist 202 is applied over the contact layer(s). Tiles 304 are dipped in resist, for example Shipley 1805 resist. Excessive resist is removed if necessary from the edge using a Q-tip, making sure the resist does not form any edge bead (especially on the pixilated face) as this would be detrimental for the pixel quality. Generally, the least possible amount of resist should remain on the pixilated face. The resist should be dried out for 10 minutes with the pixilated face kept up and horizontal.

The resist coating is hardened in step 4 by baking for 10 minutes at 90° C. This step is done to drive excess solvent out of the resist. The tile is now prepared for lithography exposure.

Figure 3E:
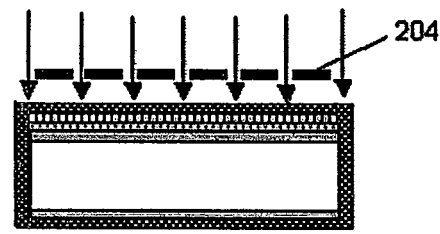

In step 5, as shown in FIG. 3E a pixel pattern is formed on the rear side of the tile 304 by photolithography. A UV mask 204 is aligned over the CZT tile surface, and the positive resist is exposed to UV. The direct lithography mask shades regions of the resist in a selected pixel pattern and exposes interpixel gaps to UV radiation. A contact mask is shown but other methods will work as well, such as proximity and projection masks. A glass plate is placed on top making sure that the glass plate is horizontal. This ensures uniform contact between the tile and the mask. For the exemplary resist, exposure by a UV lamp (365 nm wavelength) for several minutes is suitable. If desired, a negative resist may be used instead of the positive resist (in which case, the exposure mask's transparent and opaque regions are reversed).

Figure 3F:
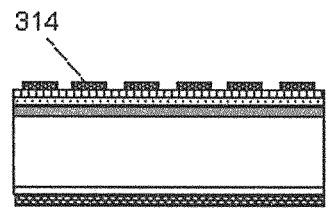

In step 6 shown in FIG. 3F, the exposed photoresist is developed. The resist developer (for example Microposit developer, MF-319) should cover the tile(s). The tiles are placed into the developer with the pixilated side facing up, developed for 2 minutes and the tile(s) are removed from the developer and rinsed in de-ionized water. The UV exposed resist is removed, in preparation for creating the interpixel gap.

In step 7 the remaining resist pixel pattern 314 is baked for 20 minutes at 90° C. This step is done to harden the resist further.

Figure 3G:
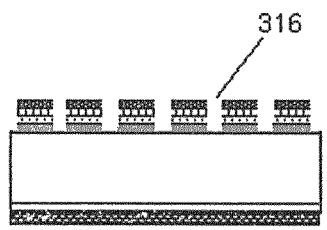

In step 8, shown in FIG. 3G, the exposed contact regions 316 (not covered by the pixel resist pattern 314) are etched. For the example contact materials, the following etching solution is suitable for etching through either just the primary contact layer or the optional three-layer contact. A 2% Br-Ethanol Glycol (BrEG) solution is prepared by pouring a 25 ml of Ethylene Glycol into a plastic beaker, then 0.5 ml of Bromine is added using a disposable pipette. Using the same pipette, the solution is mixed thoroughly until it becomes uniform. However, a different pipette or mixing device may also be used. Etching is conducted for approximately 3 minutes. This etching is done to remove unmasked interpixel contact material. To open the interpixel gap to achieve clean interpixel gaps, active spray agitation is performed. Disposable pipettes can be used to create Br-EG constant flow to agitate for better etching. However, a different pipette or agitation or mixing device may also be used. The spray etching technique should rapidly remove contact material flakes from the interpixel gaps, resulting in high interpixel resistance. The tiles are removed from the etchant and rinsed in deionized water.

Figure 3H:
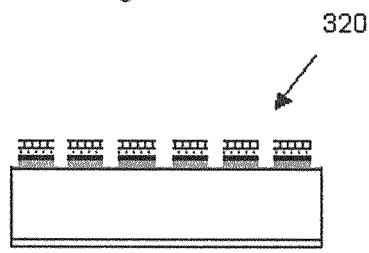

In step 9 shown in FIG. 3H, the remaining resist is stripped using an acetone bath, resulting in tile 320 with a pixel array of contacts. No photoresist therefore remains on the CdTe or CdZnTe detector since it is usually a hygroscopic material that in time would absorb humidity and deteriorate the detector performance.

The overall combination of depositing a metal layer having a work function greater than or equal to about 4.8 eV, such as gold, over the rear substrate surface, depositing a metal layer having a work function less than about 4.5 eV, such as indium, over the front surface, direct photolithography and the etching process results in the improved device performance with minimal leakage current.

Figure 3I:
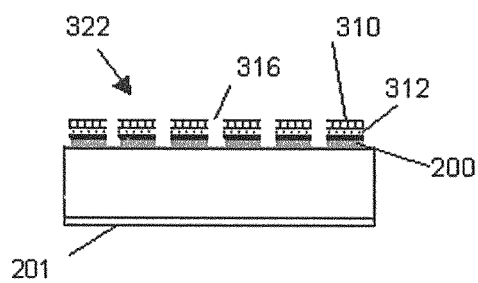

In optional step 10 shown in FIG. 3I, the primary contact material (in this example gold) on the side of the tile 305 of the fabricated CZT device 322 is removed by side polishing. For example, the side of the tile(s) are first polished with 1200 grit then with 0.3 micron as fine polish. An alternate embodiment could, in step 1, mask the sides of the CZT tile instead of depositing gold on the sides. For this reason, the side contact removal step 10 may be optional. The resulting fabricated CZT device has a cathode electrode 201 remaining on a front side, a pixilated anode electrode array formed of a primary contact layer 200 and secondary contact layers 312 and 310, separated by interpixel gaps 316 on a rear side. FIG. 3I illustrates the multi-layer pixels as being identical width in cross-section for illustrative purpose.

EXAMPLES

Ohmicity is typically exhibited by a linear current-voltage (I-V) relationship. Indium as the cathode electrode material exhibits greater ohmicity as compared to gold. As shown in FIGS. 4-7, current was measured at the cathode between 0-5 V for comparative devices and exemplary embodiments of the present invention with and without being irradiation by a Co-57 source. A linear regression analysis was performed with $R^2$ which is used to determine the linearity of the curve. It is noted that a maximum of $R^2=1$ represents a perfectly linear curve and therefore, perfect ohmic character.

Figure 4:
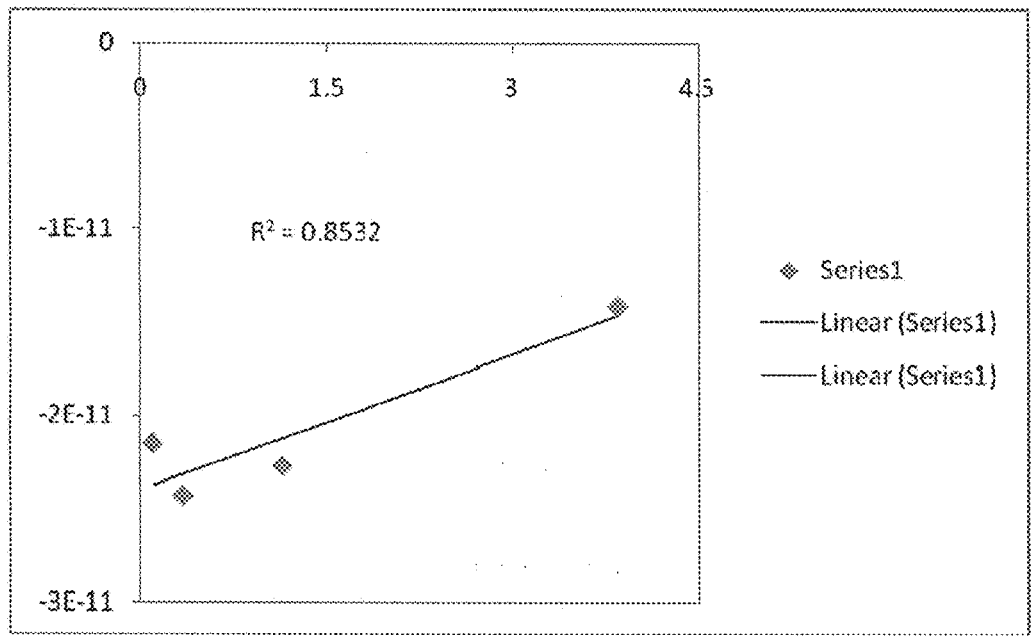
FIG. 4 is a graph showing I-V characteristics of a comparative device having a cathode comprising gold, and not exposed to radiation.
Figure 5:
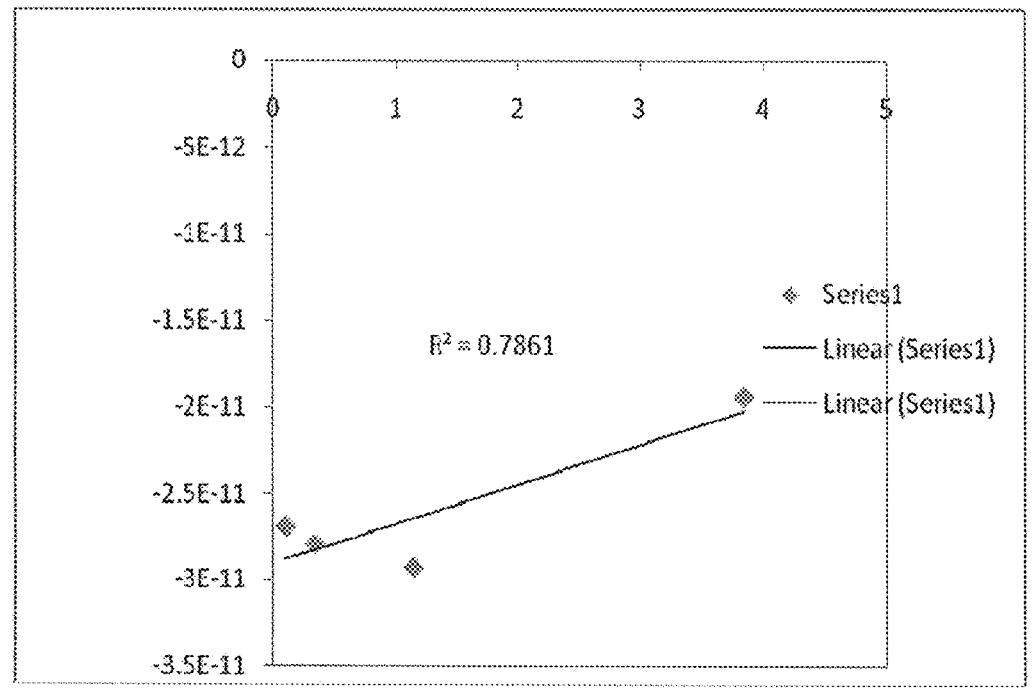
FIG. 5 is a graph showing I-V characteristics of a comparative device having a cathode comprising gold, and exposed to radiation.

As shown in FIG. 4, a regression analysis indicates that a comparative device comprising gold as the cathode electrode material and not exposed to radiation from a Co-57 source results in an $R^2$ value equal to 0.8532. As shown in FIG. 5, when the device of FIG. 4 is irradiated, a regression analysis of the I-V relationship shows a resulting $R^2$ value equal to 0.7861 which indicates that ohmicity of the gold cathode has decreased.

Figure 6:
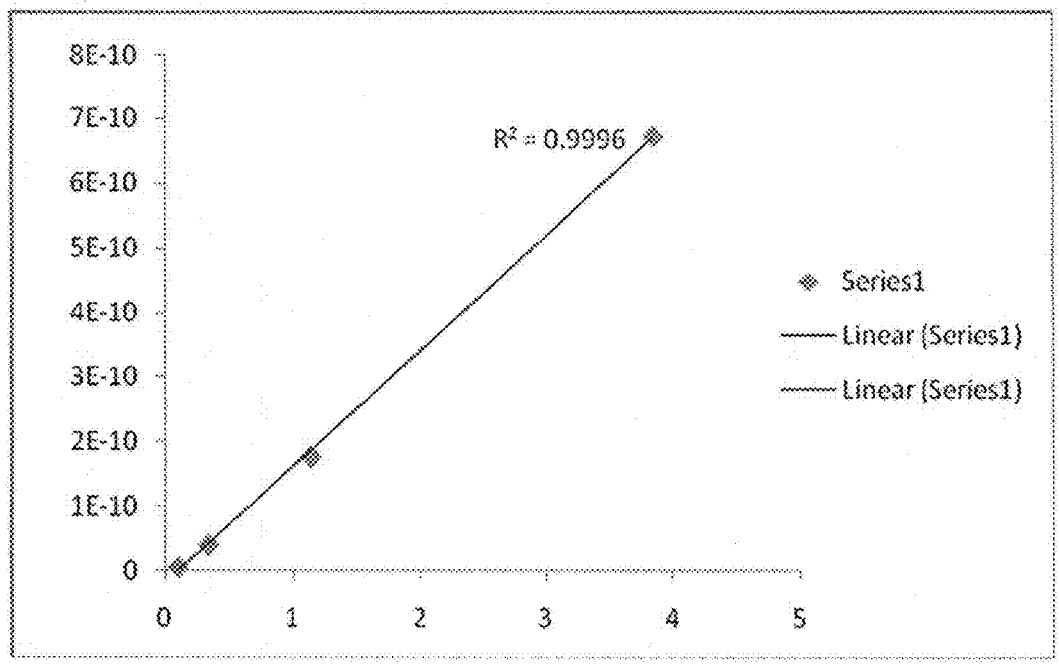
FIG. 6 is a graph showing I-V characteristics of an embodiment of the present invention having a cathode comprising indium, and not exposed to radiation.
Figure 7:
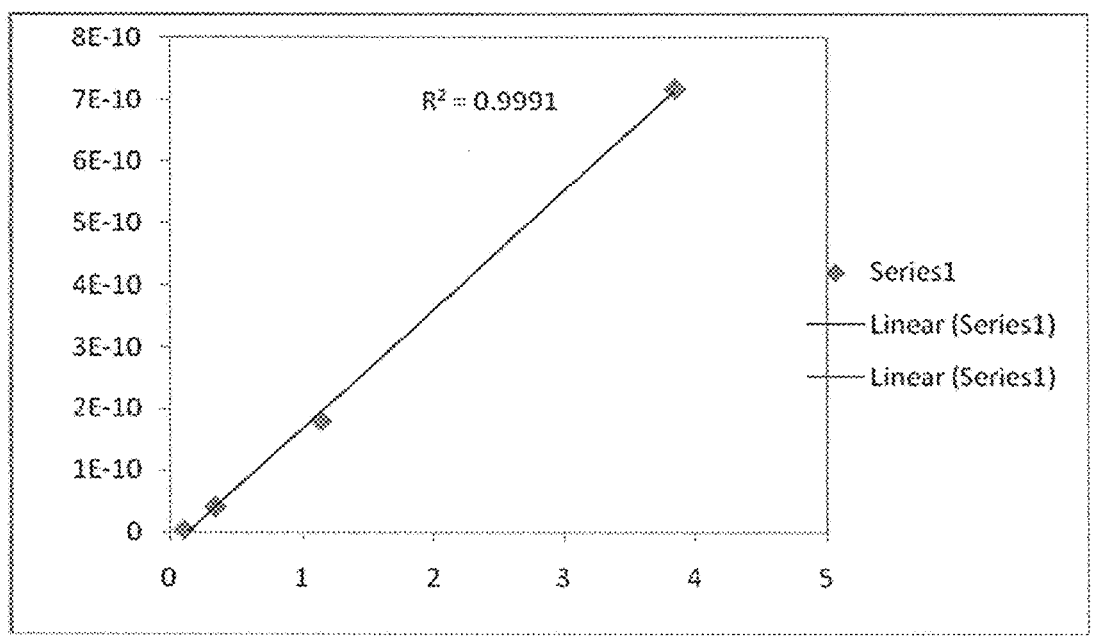
FIG. 7 is a is a graph showing I-V characteristics of an embodiment of the present invention having a cathode comprising indium, and exposed to radiation

As shown in FIG. 6, a regression analysis shows that an exemplary device comprising indium as the cathode electrode material and not irradiated by a Co-57 source results in an $R^2$ value equal to 0.9996 indicative of a high degree of linearity for the I-V relationship. As shown in FIG. 7, when the device of FIG. 6 is exposed to radiation, a regression analysis indicates that ohmicity of the indium cathode decreases only very slightly resulting $R^2$ value equal to 0.9991, still indicative of a high degree of linearity and therefore, Ohmic character.

It is clear from FIGS. 4-7 that by replacing gold as the cathode electrode material with indium, the embodiments of the present invention offer the benefits of enhanced charge collection when operated as a radiation detector for example.

In order to improve the photo-peak counts, the inventors have discovered various configurations to achieve improved sensitivity of the detectors. For example by changing the material of one of the electrodes, namely by changing the cathode electrode material from gold to indium, the result is increased electrode ohmicity. Also, by changing the active volume of the detector, for example by decreasing the interpixel gap width, an improved device performance results.

To achieve these results, radiation detectors comprising a semiconductor substrate having opposing front and rear surfaces, a cathode electrode located on the front surface of said semiconductor substrate configured so as to receive radiation, and a plurality of anode electrodes formed on the rear surface of said semiconductor substrate were manufactured. Various elements of the device were changed for a particular experimental run. For example, the interpixel gap was changed from between 600 μm to 460 μm, maintaining the pitch at 2.46 mm, on a detector with gold cathode and anode electrodes. Subsequently, keeping the pixilation on the anode untouched, the cathode was polished off, and metalized with indium. As the last step, the cathode was protected, and the anode was re-fabricated with 300 μm interpixel gap.

The following are non-limiting examples detailing particular device configurations of the present radiation detector devices of the embodiments of the invention:

Comparative Example 1

In Cathode and Au Anode with 460 μm Interpixel Gap

As a first comparative example of a radiation detector device, a 20×20×5 $mm^3$ radiation detector device with an 8×8 pixel configuration is listed in Table 1 as CE 1. The device comprises: a semiconductor substrate having opposing front and rear surfaces, a cathode electrode comprising gold located on the front surface of said semiconductor substrate configured so as to receive radiation, and a plurality of anode electrodes comprising gold formed on the rear surface of said semiconductor substrate. The plurality of anode electrodes are formed as pixels having an interpixel gap width between each pixel of about 600 μM. The anode and cathode electrodes are electrically connected to a voltage source which provides a means for applying forward-bias electric potential of about 400 V while a Co-57 source is placed 25 mm from the cathode.

Comparative Example 2

In Cathode and Au Anode with 300 μm Interpixel Gap

As a second comparative example of a radiation detector device, a 20×20×5 $mm^3$ radiation detector device with an 8×8 pixel configuration is listed in Table 1 as CE. The device comprises: a semiconductor substrate having opposing front and rear surfaces, a cathode electrode comprising gold located on the front surface of said semiconductor substrate configured so as to receive radiation, and a plurality of anode electrodes comprising gold formed on the rear surface of said semiconductor substrate. The plurality of anode electrodes are formed as pixels having an interpixel gap width between each pixel of about 460 μm. The anode and cathode electrodes are electrically connected to a voltage source which provides a means for applying forward-bias electric potential of about 400 V while a Co-57 source is placed 25 mm from the cathode.

Example 1

In Cathode and Au Anode with 460 μm Interpixel Gap

As a first example of a non-limiting embodiment of the present invention, a 20×20×5 $mm^3$ radiation detector device with an 8×8 pixel configuration is listed in Table 1. The device of Ex 1 comprises: a semiconductor substrate having opposing front and rear surfaces, a cathode electrode comprising indium located on the front surface of said semiconductor substrate configured so as to receive radiation, and a plurality of anode electrodes comprising gold formed on the rear surface of said semiconductor substrate. The plurality of anode electrodes are formed as pixels having an interpixel gap width between each pixel of about 460 μm. The anode and cathode electrodes are electrically connected to a voltage source which provides a means for applying forward-bias electric potential of about 400 V while a Co-57 source is placed 25 mm from the cathode.

Example 2

In Cathode and Au Anode with 300 μm Interpixel Gap

As a second example of another non-limiting embodiment of the present invention, a 20×20×5 mm$^3$ radiation detector device with an 8×8 pixel configuration is listed in Table 1. The device of Ex 2 comprises: a semiconductor substrate having opposing front and rear surfaces, a cathode electrode comprising indium located on the front surface of said semiconductor substrate configured so as to receive radiation, and a plurality of anode electrodes comprising gold formed on the rear surface of said semiconductor substrate. The plurality of anode electrodes are formed as pixels having an interpixel gap width between each pixel of about 300 μm. The anode and cathode electrodes are electrically connected to a voltage source which provides a means for applying forward-bias electric potential of about 400 V while a Co-57 source is placed 25 mm from the cathode. It is noted that the same Co-57 source was used for all measurements, the measurements were made within a few weeks of each other, and the measurements were taken based on a source strength of about 17 μCi.

TABLE 1

| Example | Interpixel gap (μm) | Cathode/Anode Electrode Material | Bias (Volts) | Average photo-peak counts of center pixels | % Increase over adjacent configuration |
|---|---|---|---|---|---|
| CE 1 | 600 | Au/Au | 400 | 2437 | — |
| CE 2 | 460 | Au/Au | 400 | 2726 | 12 |
| Ex 1 | 460 | In/Au | 400 | 3023 | 11 |
| Ex 2 | 300 | In/Au | 400 | 3317 | 10 |

Between the configurations of CE 1 and CE 2 as shown in Table 1, an average increase in photo-peak counts of 12% is observed.

Between the configurations of CE 2 and Ex 1 as shown in Table 1, an average increase in photo-peak counts of 11% is observed.

Between the configurations of Ex 1 and Ex 2 as shown in Table 1, an average increase in photo-peak counts of 10% is observed.

The results shown in Table 1 may be summed up as an effective increase in photo-peak counts of 30-50% in advancing the configuration of CE 1 to that of Ex 2.

Table 2 shows the change in the photo-peak counts of the center pixels between the configurations of CE 1 and CE 2 for various radiation source strengths. In the experiments yielding the results shown in Table 2, only the center pixels are considered to eliminate the edge effect from the analysis as the edge pixels did not show the expected change when the radiation source strength was doubled. As shown in Table 2, an increase in the photo-peak counts ranging from 2-23% results when the interpixel gap is changed from a width of 600 μm to 460 μm. This indicates that reducing the interpixel gap, while maintaining the other aspects of configuration, such as pitch, is advantageous to enhance the sensitivity of the detector.

TABLE 2

| Example | Configuration | Photo-peak counts | % Change |
|---|---|---|---|
| CE 1 | Au—Au 600 μm | 2650 | — |
| CE 2 | Au—Au 460 μm | 2690 | 2 |
| CE 1 | Au—Au 600 μm | 1658 | — |
| CE 2 | Au—Au 460 μm | 2000 | 21 |
| CE 1 | Au—Au 600 μm | 2913 | — |
| CE 2 | Au—Au 460 μm | 3113 | 7 |
| CE 1 | Au—Au 600 μm | 2529 | — |
| CE 2 | Au—Au 460 μm | 3102 | 23 |

In the next stage, the cathode electrode of the four 460 μm interpixel gap width detectors was changed to In. This was done by maintaining the fabrication by protecting the anode, and suspending the cathode in an electroless In solution. Table 3 shows the results of this change in the configuration.

TABLE 3

| Example | Configuration | Photo-peak counts | % Change |
|---|---|---|---|
| CE 2 | Au—Au 460 μm | 2690 | — |
| Ex 1 | In—Au 460 μm | 3230 | 20 |
| CE 1 | Au—Au 460 μm | 2000 | — |
| Ex 1 | In—Au 460 μm | 2827 | 41 |
| CE 1 | Au—Au 460 μm | 3113 | — |
| Ex 1 | In—Au 460 μm | 3392 | 9 |
| CE 1 | Au—Au 460 μm | 3102 | — |
| Ex 1 | In—Au 460 μm | 2644 | −14 |

In the final stage, the anode electrode of the four detectors was re-fabricated with a smaller interpixel gap of 300 μm. Table 4 shows the results of this step. An increase in photo-peak counts of 7-17% is seen with this change. This indicates that the 300 μm interpixel gap is the best for improvement of sensitivity for this particular detector configuration. In general, the gap width may range from 100-500 microns, such as 200-400 microns, depending on other detector materials and dimensions.

TABLE 4

| Example | Configuration | Photo-peak counts | % Change |
|---|---|---|---|
| Ex 1 | In—Au 460 μm | 3230 | — |
| Ex 2 | In—Au 300 μm | 3522 | 9 |
| Ex 1 | In—Au 460 μm | 2827 | — |
| Ex 2 | In—Au 300 μm | 3032 | 7 |
| Ex 1 | In—Au 460 μm | 3392 | — |
| Ex 2 | In—Au 300 μm | 3622 | 7 |
| Ex 1 | In—Au 460 μm | 2644 | — |
| Ex 2 | In—Au 300 μm | 3094 | 17 |

Figure 8:
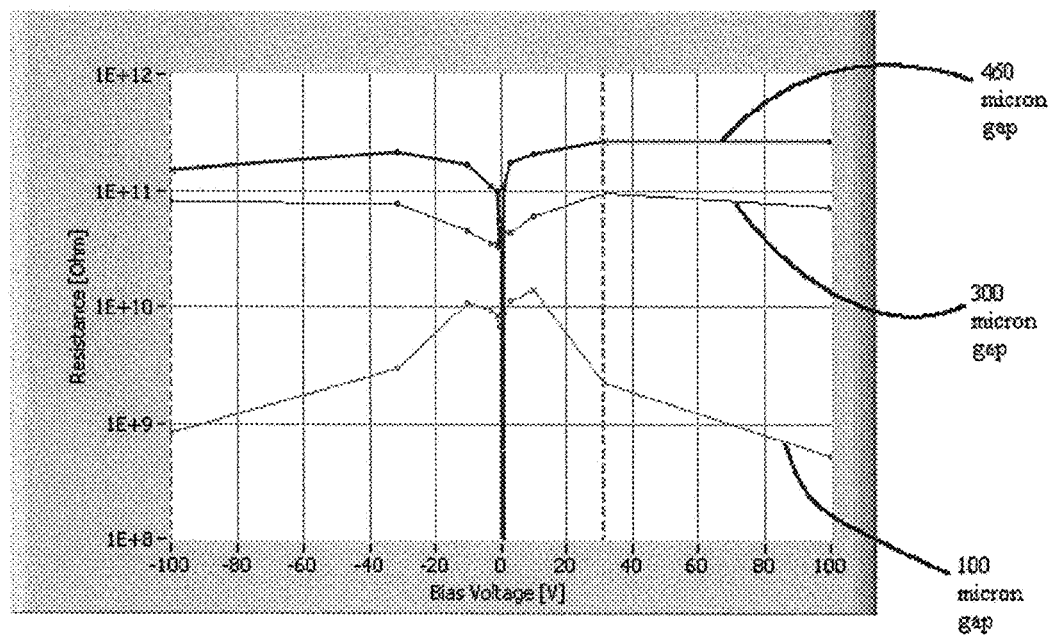
FIG. 8 is a graph showing the interpixel resistance of edge pixels at of an example embodiment of the present invention having differing interpixel gap widths.
Figure 9:
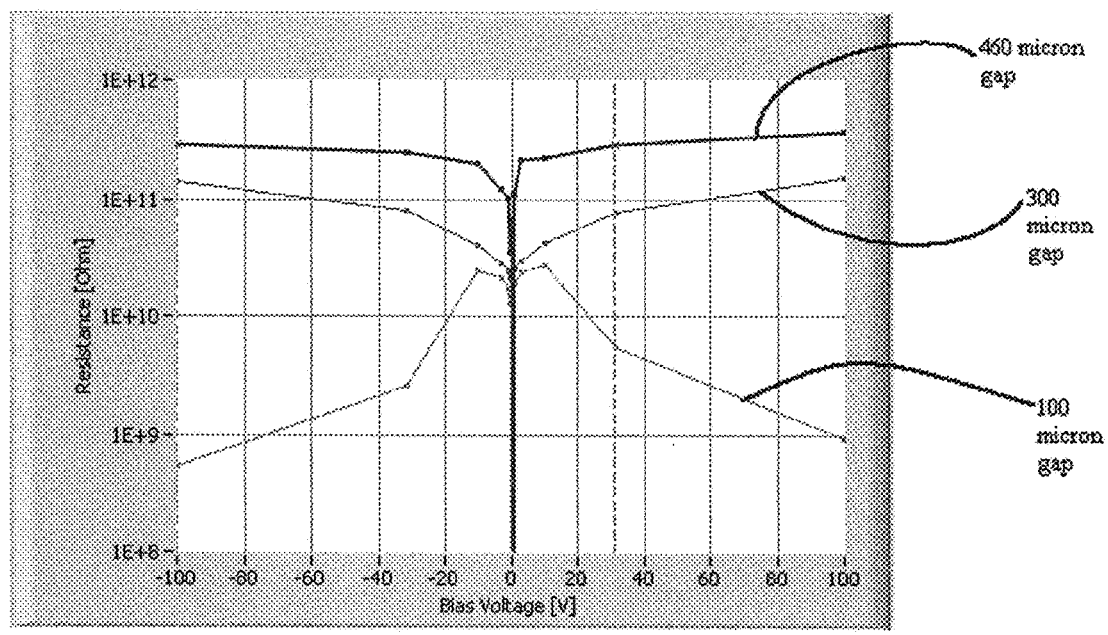
FIG. 9 is a graph showing the interpixel resistance of center pixels at of an example embodiment of the present invention having differing interpixel gap widths.

It is noted that for additional examples of the embodiments of the invention disclosed herein, the interpixel gap was reduced further to 100 μm but the measured interpixel resistance of these detectors, on average, were 2 orders of magnitude smaller than for embodiments of the present invention comprising a 460 μm interpixel gap width. In addition, the resistance profile showed a sharp decrease at higher biases indicating the possibility of electrical breakdown. For example, FIG. 8 shows a comparison of the interpixel resistance of edge pixels of the example embodiments of the present invention comprising 460 μm, 300 μm and 100 μm interpixel gap widths. FIG. 9 shows a similar comparison of the center pixels of detectors in these configurations. As noted above, the center pixels typically have the best interpixel resistance in the entire detector. Moreover, while the exemplary embodiment comprising a 300 μm interpixel gap widths exhibit marginally lower resistance than the exemplary embodiment comprising a 460 µm interpixel gap width, the resistance profile is still sufficiently flat to ensure electrical stability. Conversely, the exemplary embodiment comprising a 100 µm interpixel gap width exhibits a resistance two orders of magnitude lower than that of the exemplary embodiment comprising the 460 µm interpixel gap width, which tends to decrease very sharply towards higher biases. In other words, while the exemplary embodiment comprising a 100 µm interpixel gap width shows superior sensitivity, it has poor interpixel resistance, and the interpixel resistance is a very important factor in the energy resolution performance of radiation detectors.

APPLICATIONS

As previously mentioned, the radiation detectors discussed herein may be used for nuclear radiation detection, spectroscopy and medical imaging applications. In further embodiments, imaging devices, such as a computed tomography scanning device, may include one or more radiation detectors. Each radiation detector may include a semiconductor substrate with a cathode electrode located on its front surface and one or more anode electrodes formed on its rear surface. The work function of the cathode electrode may be lower than the work function of the anode electrode.

Figure 10:
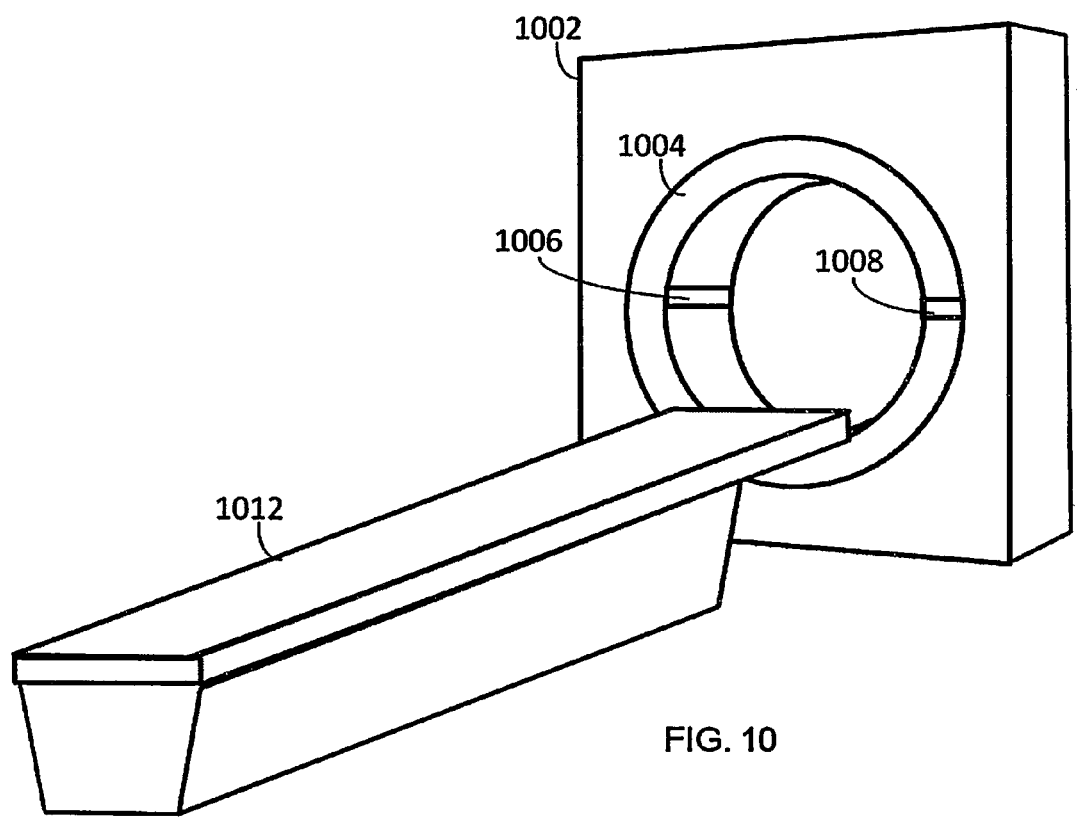
FIG. 10 is a perspective view of an embodiment imaging device.

FIG. 10 illustrates an embodiment imaging device 1002 with a rotatable gantry 1004. An x-ray source 1006, such as an x-ray tube, may be mounted on the gantry 1004. An x-ray radiation detector 1008 may also be mounted on the gantry 1004. The imaging device 1002 may be adjacent to a patient support 1012. In operation, a patient may rest on the patient support 1012 while the x-ray source 1006 emits x-rays. The x-ray radiation detector 1008 may detect x-ray radiation passing through the patient. The gantry may rotate about the patient to allow emission and detection of x-rays at multiple angles around the patient. X-ray radiation detected from multiple angles may be used, such as by an internal or external computer (not shown), to generate one or more images or three-dimensional models.

Figure 11:
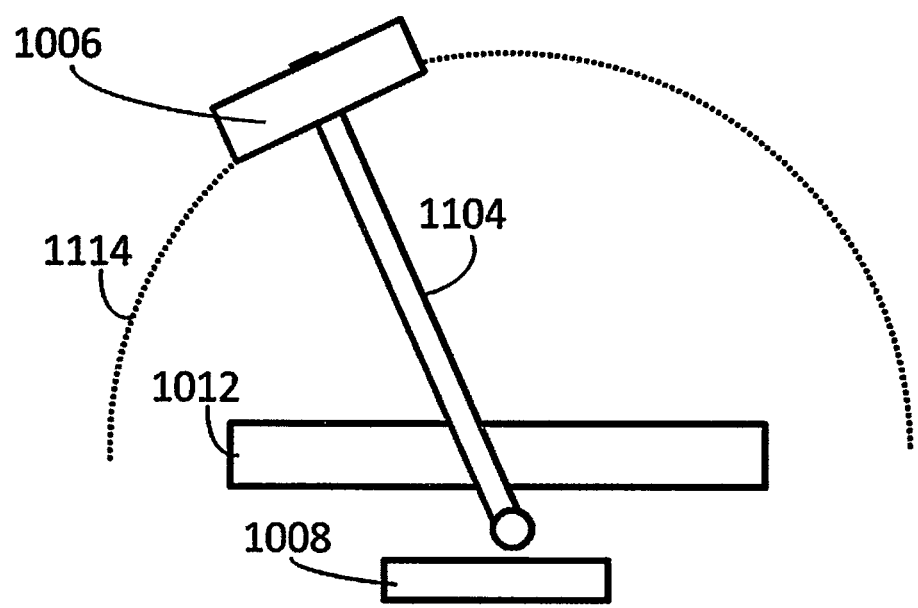
FIG. 11 is a rear view of an alternate embodiment imaging device.

In alternate embodiments, the x-ray radiation detector may be stationary and the x-ray radiation source may be mounted on a movable gantry. FIG. 11 illustrates an embodiment device including an x-ray radiation detector 1008 that is fixed in location (e.g., below or in a patient support 1012) and an x-ray source 1006 mounted on a gantry 1104. The gantry 1104 may be an arm that rotates in an arc 1114 about a pivot 1116 during an operation, such as in an arc 1114 about a patient laying on patient support 1012.

Further applications may include using radiation detectors as part of a security screening device. For example, security screening devices, such as at the entrance to certain restricted areas (e.g., airports, courthouses, museums, etc.) may be used to inspect people or object for security purposes. In various embodiments, security screening devices may include one or more radiation detectors. As discussed above, each radiation detector may include a semiconductor substrate with a cathode electrode located on its front surface and one or more anode electrodes formed on its rear surface. The work function of the cathode electrode may be lower than the work function of the anode electrode.

Figure 12:
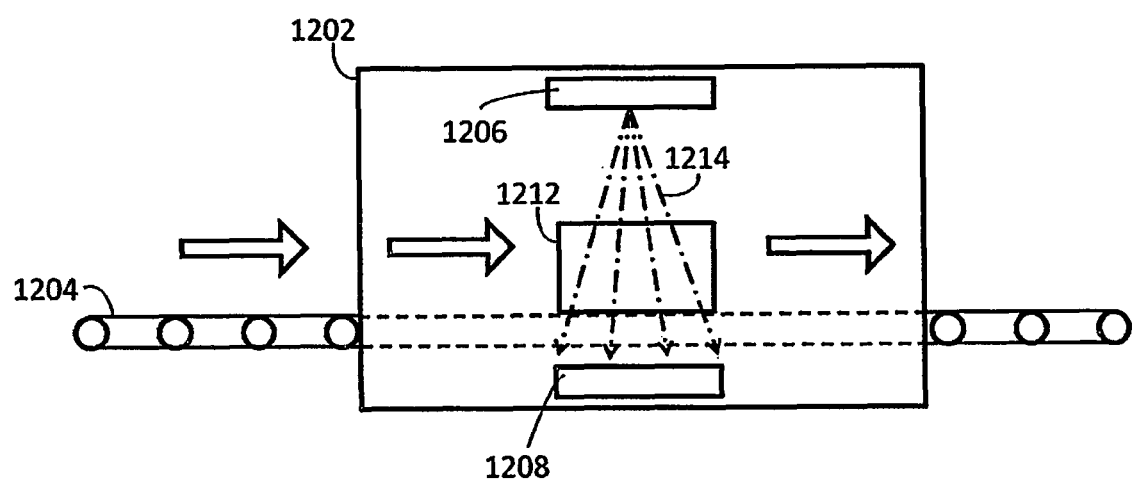
FIG. 12 is a perspective view of an embodiment security screening device.

FIG. 12 illustrates an embodiment security screening device 1202. An x-ray source 1206, such as an x-ray tube, may be mounted inside the security screening device 1202. A radiation detector 1208 may also be mounted inside. In operation, objects to be scanned 1212 (e.g., luggage, packages, etc., at an airport, bags or purses at a courthouse, etc.) may be placed on a conveyor belt 1204 and moved through the device 1202 in the direction of the arrows in FIG. 12 while the x-ray source 1206 emits x-rays 1214. The radiation detector 1208 may detect x-ray radiation passing through any objects on the conveyor belt 1204. Any radiation detected may be used to generate one or more images of the scanned object to be displayed for an operator and/or analyzed by a computer to raise an alarm if the radiation detected meets predetermined criteria, such as a predetermined minimum amount or intensity of radiation or certain patterns of radiation, such as patterns corresponding to restricted items (e.g., a pattern resembling a gun or other weapon). The radiation detector may also be used to detect any x-rays and/or gamma rays emanating from the object 1212. For example, the detector may generate an alarm (e.g., audible signal and/or an image or text on a display screen) if greater than a predetermined amount of gamma radiation is detected. Thus, the detector may be used to both image objects located in a container (e.g., luggage, bags, purses, shipping crate, packages, etc.) and to detect radiation (e.g., gamma radiation) emitted by the objects in the same container at the same time.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention. All of the publications, patent applications and patents cited herein are incorporated herein by reference in their entirety.

What is claimed is:

1. An x-ray radiation detector comprising:
   a semiconductor substrate having opposing front and rear surfaces;
   a cathode electrode located on the front surface of said semiconductor substrate configured so as to receive x-ray radiation; and
   a plurality of anode electrodes formed on the rear surface of said semiconductor substrate;
   wherein a work function of the cathode electrode material contacting the front surface of the semiconductor substrate is lower than a work function of the anode electrode material contacting the rear surface of the semiconductor substrate;
   wherein the plurality of anode electrodes are configured as pixels with an interpixel gap between each two adjacent anode electrode pixels; and
   wherein said interpixel gap width is between 300 and 500 µm.

2. The detector of claim 1, wherein the x-ray radiation detector is part of a computed tomography scanning device.

3. The detector of claim 2, wherein the x-ray radiation detector is coupled with an x-ray radiation source.

4. The detector of claim 3, wherein the x-ray radiation source and x-ray radiation detector are mounted on a rotatable gantry.

5. The detector of claim 3, wherein the x-ray radiation detector is stationary and the x-ray radiation source is mounted on a movable gantry.

6. The detector of claim 1, wherein the work function of the cathode electrode material is less than about 4.5 eV, and the work function of the anode electrode material is greater than or equal to about 4.8 eV.

7. The detector of claim 1, wherein the cathode electrode material comprises one of In, Al, and Ti.

8. The detector of claim 1, wherein the anode electrode material comprises one of Au and Pt.

9. The detector of claim 1, wherein the semiconductor substrate comprises CdTe or CZT, and the substrate lacks a p-n or p-i-n junction.

10. The detector of claim 1, further comprising an electrically conductive housing located in electrical contact with the cathode electrode.

11. The detector of claim 1, further comprising a voltage source electrically connected to the anode and the cathode electrodes.

12. The detector of claim 1, further comprising a means for applying a forward bias to the detector during operation such that the plurality of anode electrodes is maintained at a higher potential than the cathode electrode and such that a signal is collected from the anode electrodes.

13. The detector of claim 1, wherein the x-ray radiation detector is part of a security screening device.

14. The detector of claim 13, wherein the detector further comprises an x-ray radiation source.

15. A method of operating an x-ray radiation detector, comprising:
   providing an x-ray radiation detector comprising:
      a semiconductor substrate having opposing front and rear surfaces;
      a cathode electrode located on the front surface of said semiconductor substrate configured so as to receive x-ray radiation; and
      a plurality of anode electrodes formed on the rear surface of said semiconductor substrate,
      wherein a work function of the cathode electrode material contacting the front surface of the semiconductor substrate is lower than a work function of the anode electrode material contacting the rear surface of the semiconductor substrate;
   receiving x-ray radiation at the cathode electrode;
   applying a forward bias to detector to maintain the anode electrodes at a higher potential than the cathode electrode; and
   collecting a signal from the anode electrodes;
   wherein the plurality of anode electrodes are configured as pixels with an interpixel gap between each two adjacent anode electrode pixels and the signal comprises a measured current or voltage which corresponds to the radiation received at each pixel; and
   wherein said interpixel gap width is between 300 and 500 µm.

16. The method of claim 15, wherein the x-ray radiation detector is part of a computed tomography scanning device.

17. The method of claim 16, wherein the x-ray radiation detector is coupled with an x-ray radiation source and receiving x-ray radiation comprises receiving x-ray radiation from the x-ray radiation source which passes through a patient.

18. The method of claim 17, further comprising rotating a rotatable gantry, and wherein the x-ray radiation source and x-ray radiation detector are mounted on the rotatable gantry and rotate about the patient.

19. The method of claim 17, further comprising moving a mobile gantry supporting the x-ray radiation source in an arc about the patient while the x-ray radiation detector remains stationary.

20. The method of claim 15, wherein the work function of the cathode electrode material is less than about 4.5 eV, and the work function of the anode electrode material is greater than or equal to about 4.8 eV.

21. The method of claim 15, wherein the cathode electrode material comprises one of In, Al, and Ti, the anode electrode material comprises one of Au and Pt, and the semiconductor substrate comprises CdTe or CZT.

22. The method of claim 15, wherein said forward bias injects electrons from said cathode electrode material into the front surface of the semiconductor substrate.

23. The method of claim 15, wherein the x-ray radiation detector is part of a security screening device.

24. The method of claim 23, further comprising:
   passing an object on a conveyor belt; and
   irradiating the object with x-ray radiation from an x-ray source, wherein receiving x-ray radiation at the cathode electrode comprises receiving x-ray radiation at the cathode electrode from the x-ray source that passed through the object.

25. The method of claim 23, wherein the x-ray radiation detector is configured to detect gamma radiation and generate an alarm if greater than a predetermined amount of gamma radiation is detected.

* * * * *